United States Patent [19]
Amato et al.

[11] Patent Number: 6,040,488
[45] Date of Patent: Mar. 21, 2000

[54] STABILIZATION OF VINYLIDENE CHLORIDE

[75] Inventors: Domenick V. Amato, Paducah, Ky.; Earl M. Gorton, Sulphur, La.

[73] Assignee: PPG Industries Ohio, Inc., Cleveland, Ohio

[21] Appl. No.: 09/088,819

[22] Filed: Jun. 2, 1998

[51] Int. Cl.[7] .................................................. G07C 17/42
[52] U.S. Cl. ............................................................ 570/264
[58] Field of Search ............................................... 570/264

[56] References Cited

U.S. PATENT DOCUMENTS 3,494,967   2/1970   Bailey .
3,733,326   5/1973   Murrayama et al. .
5,654,434   8/1997   Pastor et al. .

FOREIGN PATENT DOCUMENTS

845458 A1   6/1998   European Pat. Off. .
WO 98/02400   1/1998   WIPO .

*Primary Examiner*—Alan Siegel
*Attorney, Agent, or Firm*—George D. Morris

[57] ABSTRACT

Vinylidene chloride is stabilized with free radical stabilizer having at least one 2,2,6,6-tetra(lower alkyl)-1-piperidinyloxy-yl free radical group.

21 Claims, No Drawings

STABILIZATION OF VINYLIDENE CHLORIDE

Vinylidene chloride [CAS 75-35-4] is a monomer which is useful in producing many polymers, especially saran. Vinylidene chloride, however, tends to spontaneously polymerize in storage unless it is stabilized with a stabilizing amount of stabilizer. Although several stabilizers have been used for this purpose, hydroquinone monomethyl ether [CAS 150-76-5] has become the generally accepted stabilizer of choice.

A class of free radicals has now been found which is more efficient in stabilizing vinylidene chloride from spontaneous polymerization than hydroquinone monomethyl ether. Due to this greater stabilization efficiency, less free is radical stabilizer is required to accomplish the desired stabilization than is the situation for hydroquinone monomethyl ether. This is advantageous to users of the vinylidene chloride because polymerization reactions will not require as much initiator to override the stabilizer. Accordingly, the invention is a composition comprising vinylidene chloride and a stabilizing amount of free radical stabilizer having at least one 2,2,6,6-tetra(lower alkyl)piperidinyloxy-yl free radical group.

The lower alkyl groups may be the same or they may be different, but preferably they are the same. The lower alkyl groups usually employed are methyl or ethyl, although lower alkyl groups having more than two carbon atoms are within contemplation. The preferred lower alkyl group is methyl.

The 2,2,6,6-tetra(lower alkyl)piperidinyloxy-yl free radical group is usually the 2,2,6,6-tetra(lower alkyl) piperidinyloxy-4-yl free radical group, but the 2,2,6,6-tetra (lower alkyl)piperidinyloxy-3-yl free radical group may be used when desired. 2,2,6,6-Tetra(lower alkyl) piperidinyloxy-yl free radical groups may be attached to hydrogen, hydroxyl, oxo, or to a parent compound as a substituent. The preferred parent compounds are the monocarboxylic acids and the dicarboxylic acids in which case the free radical stabilizers are esters. The monocarboxylic acids are ordinarily aliphatic or aromatic.

In many instances the aliphatic monocarboxylic acids are saturated and contain from 1 to 18 carbon atoms. Frequently the aliphatic monocarboxylic acids contain from 2 to 12 carbon atoms. From 3 to 8 carbon atoms is preferred.

Of the aromatic monocarboxylic acids, benzoic acid is preferred.

Usually the dicarboxylic acids are saturated and contain from 2 to 13 carbon atoms. Often the saturated dicarboxylic acid contains from 4 to 12 carbon atoms. In many instances the saturated dicarboxylic acid contains from 8 to 12 carbon atoms. The particularly preferred saturated dicarboxylic acid is sebacic acid which contains 10 carbon atoms.

The free radical stabilizers and methods for their preparation are generally known. Examples of suitable of free radical stabilizers include:

2,2,6,6-tetramethyl-1-piperidinyloxy [CAS 2564-83-2];

2,2,6,6-tetramethyl-4-hydroxy-1-piperidinyloxy [CAS 2226-96-2];

2,2,6,6-tetramethyl-4-oxo-1-piperidinyloxy [CAS 2896-70-0];

2,2,6,6-tetramethyl-4-((methylsulfonyl)oxy)-1-piperidinyloxy [CAS 35203-66-8];

2,2,6,6-tetramethyl-1-piperidinyloxy-4-yl) benzoate [CAS 3225-26-1]; and bis(2,2,6,6-tetramethyl-1-piperidinyloxy-4-yl) sebacate [CAS 2516-92-9]

The amount of free radical stabilizer which is present in the compositions of the present invention may vary considerably, but ordinarily the free radical stabilizer is present in an amount in the range of from 1 to 200 parts per million parts of the composition, by weight. In many instances the free radical stabilizer is present in an amount in the range of from 1 to 100 parts per million parts of the composition, by weight. Often the free radical stabilizer is present in an amount in the range of from 2 to 50 parts per million parts of the composition, by weight. Frequently the free radical stabilizer is present in an amount in the range of from 5 to 30 parts per million parts of the composition, by weight. From 10 to 20 parts per million parts of the composition by weight is preferred.

The amount of vinylidene chloride present in the composition may vary considerably. Other ethylenically unsaturated monomers may optionally be present when desired. Usually vinylidene chloride constitutes at least 90 percent by weight of the composition of the invention. Frequently vinylidene chloride constitutes at least 95 percent by weight of the composition. At least 99 percent by weight is preferred.

The invention is further described in conjunction with the following example which is to be considered illustrative rather than limiting, and in which all parts are parts by weight and all percentages are percentages by weight unless otherwise specified. The free radical stabilizers are abbreviated according to the following key:

| Free Radical Stabilizer | Abbreviation |
|---|---|
| 2,2,6,6-Tetramethyl-1-piperidinyloxy [CAS 2564-83-2] | Inhibitor A |
| Bis(2,2,6,6-tetramethyl-1-piperidinyloxy-4-yl) sebacate [CAS 2516-92-9] | Inhibitor B |
| Hydroquinone monomethyl ether [CAS 150-76-5] | HQMME |

EXAMPLE

A first stock solution was formed by admixing 0.59 gram of Inhibitor A and 570.21 grams inhibitor-free vinylidene chloride.

A second stock solution was formed by admixing 0.55 gram of Inhibitor B and 569.85 grams inhibitor-free vinylidene chloride.

A third stock solution was formed by admixing 0.57 gram of Control Inhibitor and 575.14 grams inhibitor-free vinylidene chloride.

To each of a series of clear glass sample bottles was added 100 milliliters of nitrogen-padded, inhibitor-free vinylidene chloride. To most of the sample bottles was added 0.20, 0.50, or 1.50 milliliters of one of the stock solutions. The bottles were padded with nitrogen and sealed. One of the clear glass sample bottles containing the nitrogen-padded, inhibitor-free vinylidene chloride, but not containing any added inhibitor was padded with nitrogen and sealed. Another of the clear glass sample bottles containing the nitrogen-padded, inhibitor-free vinylidene chloride, but not containing any added inhibitor was padded with air and sealed. Table 1 shows the nominal and actual inhibitor concentrations of the test solutions in the bottles, where "ppm" is a abbreviation for parts of inhibitor per million parts of total composition, by weight.

TABLE 1

| Inhibitor Concentration, ppm | | | |
|---|---|---|---|
| Nominal | Inhibitor A | Inhibitor B | HQMME |
| 2 | 2.06 | 1.92 | 1.98 |
| 5 | 5.14 | 4.80 | 4.93 |
| 15 | 15.28 | 14.25 | 14.63 |

The sealed bottles were stored in the dark and periodically inspected for polymer formation. On the first day, polymer formation was observed in both the sample containing no inhibitor which was padded with nitrogen and in the sample containing no inhibitor which was padded with air. The number of days until polymer formation for the remaining samples is shown in Table 2.

TABLE 2

| Days Until Polymer Formation | | | |
|---|---|---|---|
| NIC, ppm | Inhibitor A | Inhibitor B | HQMME |
| 2 | 37 | 22 | 13 |
| 5 | 119 | 100 | 28 |
| 15 | >233 | >233 | >233 |

In Table 2, "NIC" is an abbreviation for "Nominal Inhibitor Concentration". The test was discontinued after 233 days. No polymer formation was observed after 233 days in any of the samples having a Nominal Inhibitor Concentration of 15 ppm; however color was visible in the sample stabilized with HQMME after 189 days.

Although the present invention has been described with reference to specific details of certain embodiments thereof, it is not intended that such details should be regarded as limitations upon the scope of the invention except insofar as they are included in the accompanying claims.

We claim:

1. A composition comprising vinylidene chloride and a stabilizing amount of free radical stabilizer having at least one 2,2,6,6-tetra(lower alkyl)-1-piperidinyloxy-yl free radical group.

2. The composition of claim 1 wherein the 2,2,6,6-tetra (lower alkyl)-1-piperidinyloxy-yl free radical group is the 2,2,6,6-tetramethyl-1-piperidinyloxy-yl free radical group.

3. The composition of claim 1 wherein the 2,2,6,6-tetra (lower alkyl)-1-piperidinyloxy-yl free radical group is the 2,2,6,6-tetramethyl-1-piperidinyloxy-4-yl free radical group.

4. The composition of claim 1 wherein the free radical stabilizer is 2,2,6,6-tetramethyl-1-piperidinyloxy free radical stabilizer.

5. The composition of claim 1 wherein the free radical stabilizer is 2,2,6,6-tetramethyl-4-hydroxy-1-piperidinyloxy free radical stabilizer.

6. The composition of claim 1 wherein the free radical stabilizer is 2,2,6,6-tetramethyl-4-oxo-1-piperidinyloxy free radical stabilizer.

7. The composition of claim 1 wherein the free radical stabilizer is 2,2,6,6-tetramethyl-4-((methylsulfonyl)oxy)-1-piperidinyloxy free radical stabilizer.

8. The composition of claim 1 wherein the free radical stabilizer is 2,2,6,6-tetramethyl-1-piperidinyloxy-4-yl) benzoate free radical stabilizer.

9. The composition of claim 1 wherein the free radical stabilizer is bis(2,2,6,6-tetramethyl-1-piperidinyloxy-4-yl) ester of saturated dicarboxylic acid free radical stabilizer.

10. The composition of claim 9 wherein the saturated dicarboxylic acid contains from 2 to 13 carbon atoms.

11. The composition of claim 1 wherein the free radical stabilizer is bis(2,2,6,6-tetramethyl-1-piperidinyloxy-4-yl) sebacate free radical stabilizer.

12. The composition of claim 1 wherein the free radical stabilizer is present in an amount in the range of from 1 to 200 parts per million parts of the composition, by weight.

13. The composition of claim 1 wherein the free radical stabilizer is present in an amount in the range of from 1 to 100 parts per million parts of the composition, by weight.

14. The composition of claim 1 wherein the free radical stabilizer is present in an amount in the range of from 2 to 50 parts per million parts of the composition, by eight.

15. The composition of claim 1 wherein the free radical stabilizer is present in an amount in the range of from 5 to 30 parts per million parts of the composition, by weight.

16. The composition of claim 1 wherein the free radical stabilizer is present in an amount in the range of from 10 to 20 parts per million parts of the composition, by weight.

17. The composition of claim 1 wherein vinylidene chloride constitutes at least 90 percent by weight of the composition.

18. The composition of claim 1 wherein vinylidene chloride constitutes at least 95 percent by weight of the composition.

19. The composition of claim 1 wherein vinylidene chloride constitutes at least 99 percent by weight of the composition.

20. The composition of claim 1 wherein:

(a) vinylidene chloride constitutes at least 99 percent by weight of the composition;

(b) the free radical stabilizer is 2,2,6,6-tetramethylpiperidinyloxy free radical stabilizer; and (c) the 2,2,6,6-tetramethylpiperidinyloxy free radical stabilizer is present in an amount in the range of from 10 to 20 parts per million parts of the composition, by weight.

21. The composition of claim 1 wherein:

(a) vinylidene chloride constitutes at least 99 percent by weight of the composition;

is (b) the free radical stabilizer is bis(2,2,6,6-tetramethylpiperidinyloxy-4-yl) sebacate free radical stabilizer; and (c) the bis(2,2,6,6-tetramethylpiperidinyloxy-4-yl) sebacate free radical stabilizer is present in an amount in the range of from 10 to 20 parts per million parts of the composition, by weight.

* * * * *